United States Patent

Thunberg

[11] Patent Number: 6,106,152
[45] Date of Patent: Aug. 22, 2000

[54] X-RAY EXPOSURE SYSTEM AND METHOD FOR OPERATING SAME

[75] Inventor: Stefan Thunberg, Stockholm, Sweden

[73] Assignee: Siemens Elema AB, Solna, Sweden

[21] Appl. No.: 09/012,593

[22] Filed: Jan. 23, 1998

[30] Foreign Application Priority Data

Jan. 30, 1997 [SE] Sweden ................................. 9700277

[51] Int. Cl.⁷ ..................................................... G21K 1/04
[52] U.S. Cl. ......................................... 378/205; 378/98.8
[58] Field of Search .................................. 378/205, 98.8, 378/151, 150

[56] References Cited

U.S. PATENT DOCUMENTS

| | | | |
|---|---|---|---|
| 4,092,544 | 5/1978 | Grim | 378/206 |
| 4,167,675 | 9/1979 | Stödberg et al. | 378/206 |
| 5,048,070 | 9/1991 | Maehama et al. | 378/197 |
| 5,287,396 | 2/1994 | Stegehuis | 378/98.2 |
| 5,299,250 | 3/1994 | Styrnol et al. | 378/19 |
| 5,412,704 | 5/1995 | Horbaschek | 378/98.2 |
| 5,844,962 | 12/1998 | Kunert | 378/206 |

*Primary Examiner*—David P. Porta
*Assistant Examiner*—Drew A. Dunn
*Attorney, Agent, or Firm*—Hill & Simpson

[57] ABSTRACT

An X-ray exposure apparatus has an x-ray radiator having an X-ray tube provided with collimators for the limitation of a radiated X-ray beam. The x-ray radiator can be displaced translationally and/or rotated angularly for the orientation in space of the radiation beam. A digital image receiver has a number pixels, and there is no mechanical connection between the image receiver and the x-ray radiator. A sampling unit samples the signals of the image receiver in order to determine which pixels are irradiated by the radiation beam in a test exposure and dependent thereon, control signals are emitted to adjustment unit and/or to a radiator collimator displacement and/or rotation control unit, which, dependent on the control signals, adjust the collimators or the position of the x-ray radiator in relation to the image receiver, and/or move the x-ray radiator parallel to the image receiver for the optimal adjustment of the beam thereto. Alternatively, the signals from the sampling unit can be used to produce on a display screen an image of the radiation field on the image receiver, so that, using this image, an optimal adjustment of the radiation field to the image plate is enabled by means of manual adjustment of collimators and/or by means of manual displacement and/or orientation of the radiating head. In a test exposure of a patient, an image of the outer contours of the patient can be obtained on the display screen, together with the image of the radiation field on the image plate, after which the radiation field is matched to the outer contours of the patient using this image.

14 Claims, 5 Drawing Sheets

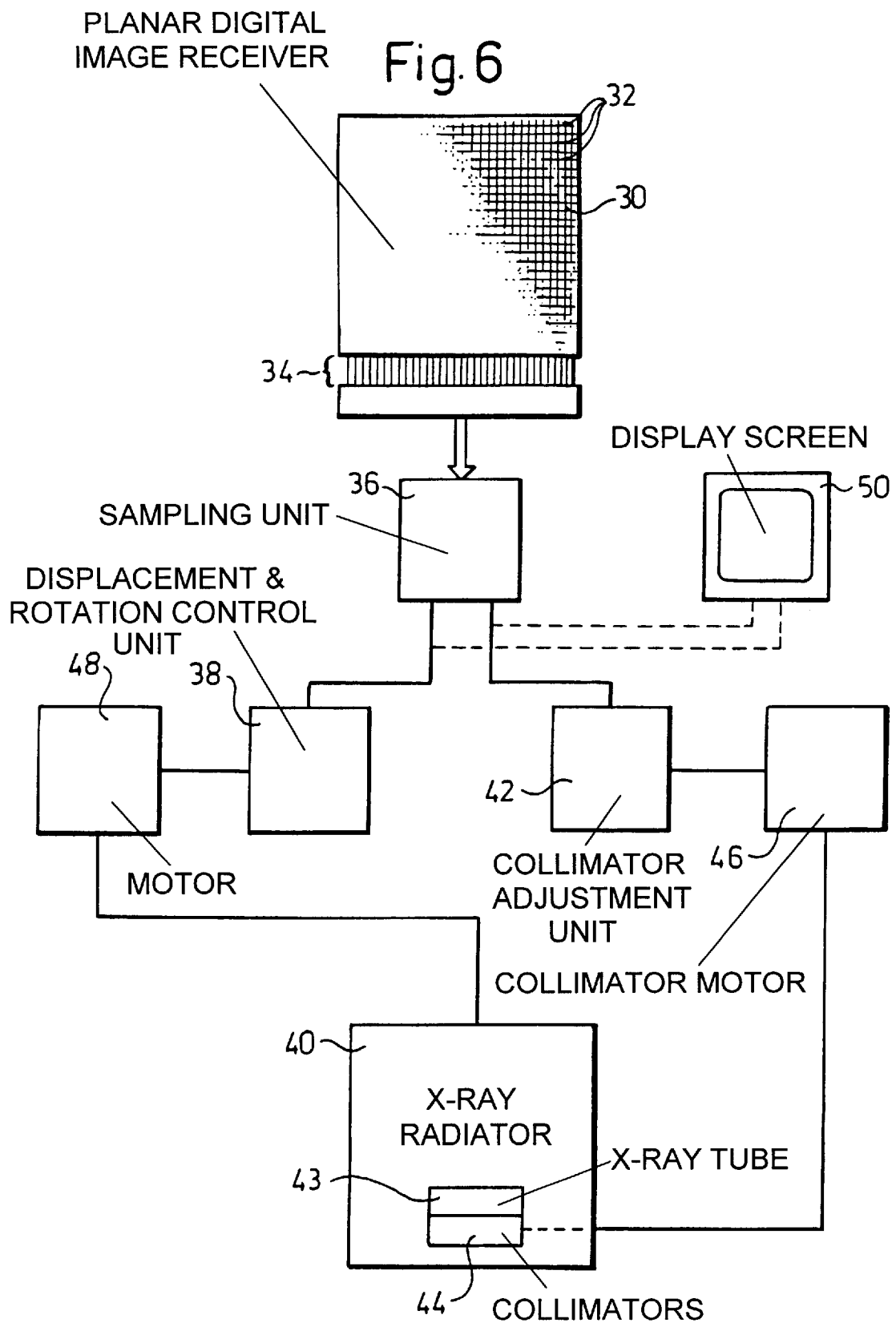

X-RAY EXPOSURE SYSTEM AND METHOD FOR OPERATING SAME

BACKGROUND OF THE INVENTION

1. Field of the Invention

The present invention is directed to an X-ray exposure system of the type having an x-ray radiator containing an X-ray tube and provided with collimators for limiting the radiated X-ray beam, in which the x-ray radiator can be displaced translationally and/or rotated angularly for orientating the radiation beam in space, as well as a planar digital image receiver having a number of pixels, with no mechanical connection between the image receiver and the x-ray radiator.

2. Description of the Prior Art

In X-ray examinations of patients, it is important for the radiation beam that is radiated by the radiation source to strike the X-ray film after passing through that part of the patient that is to be radiographed, so that an image of the exposed location is produced. A mobile X-ray apparatus, e.g. of the type described in the brochure MOBILETT Plus of the company Siemens-Elema AB, is used with a film cartridge (cassette) having no mechanical connection with the X-ray source. The film cartridge is placed under the patient, often under the mattress on which the patient is positioned. The operator then orients the radiation field as desired relative to the film cartridge. The field of radiation is often made extra large in order to avoid the risk that it will fail to cause the film. This causes unnecessarily high doses of radiation, as well as worsened image quality due to scattered radiation. Moreover, this leads to repeat exposures, due to incorrect settings of the radiation field in relation to the cartridge.

An attempt to remedy this problem is described in U.S. Pat. No. 4,092,544. In this reference, an X-ray exposure apparatus having a light source is disclosed that is connected in fixed relation to the X-ray tube and the diaphragm thereof. Furthermore, markings are arranged on a part connected fixedly to the film cartridge. The light source and the aforementioned part of the film cartridge provided with markings are arranged so that the light from the light source is not interrupted by a patient radiographed with the X-ray apparatus. By observation of the location at which the light beam from the light source strikes the part fixedly connected with the film cartridge, as well as observation of how the light beam strikes the markings, it can be determined whether the edges of the film cartridge are parallel to the outer boundaries of the X-ray beam that strikes the film cartridge, whether the central ray of the X-ray beam strikes the center of the film cartridge, and whether a desired target film distance has been set.

In U.S. Pat. No. 4,167,675, an X-ray collimator is described in which a light source is used to produce a beam of radiation whose shape and position coincides with the shape and position of the X-ray beam. By this means, a visual display of the extension and position of the X-ray beam of radiation is produced. This visual display, however, cannot be used to adjust the X-ray beam to a film cartridge in those situations wherein the region of the patient that is to be exposed is located, possibly with a mattress, between the X-ray source and the film cartridge.

SUMMARY OF THE INVENTION

An object of the present invention is to avoid the aforementioned problems associated with the orientation and adjustment of the X-ray beam relative to the image surface given digital image recording in an apparatus wherein there is no mechanical connection between the x-ray radiator and the radiation receiver.

The above object is achieved in accordance with the principles of the present invention in an x-ray exposure system having an x-ray radiator containing an x-ray tube provided with collimators for gating the x-ray beam radiated by the x-ray tube, the x-ray radiator being displaceable translationally and/or rotationally so as to orient the radiated x-ray beam in space. The x-ray exposure system also includes a planar digital image receiver, having a large number of pixels, with no mechanical connection existing between the x-ray radiator and the image receiver. A sampling (scanning) unit samples (scans) the signals from the image receiver in order to determine which pixels are irradiated by the x-ray beam in a test exposure. Dependent on the result of this sampling, control signals are produced and are supplied to at least one control unit which controls positioning of the x-ray radiator to, in turn, position the x-ray beam. The control units can include a control unit for adjusting the collimators, a control unit for translationally displacing the x-ray radiator relative to the image receiver, a control unit for rotating the x-ray radiator relative to the image receiver, and a control unit for moving the x-ray radiator toward and away from the image receiver. Optimal adjustment of the x-ray beam relative to the active surface of the image receiver is thereby achieved, i.e., the size of the x-ray beam on the active surface of the image receiver is only as large as is necessary to cover the active area (if desired) or to irradiate a region of interest of the patient (if desired).

In an X-ray exposure system according to the invention, the position of the X-ray beam on the digital image plate is thus determined by sampling the signals of the image plate in order to determine which pixels are illuminated by the radiation beam in a test exposure. This information is then used to adjust the collimators of the X-ray source or to adjust the direction and position of the radiating head in relation to the image receiver's active surface, for an optimal adjustment of the radiation beam to the image receiver surface.

In an embodiment of the system according to the invention, the adjustment of the X-ray beam to the image receiver can be automated by driving the collimators with motors, automatically controlling the motors of the collimators dependent on a sampled illumination of the image plate, and using the displacement and rotation arrangement to additionally control a motor-driven drive unit for automatically adjusting the radiating head dependent on a sampled irradiation of the image receiver's active surface.

In a further embodiment of the system according to the invention, the sampling unit is employed to determine the outer contours of a patient during a test exposure, and the adjustment and rotation arrangement is operated using control signals from the sampling unit so as to match the radiation field to the outer contours of the patient on the image receiver surface. In this way, the X-ray radiation field can be limited so that only the part of the image receiver surface that is of interest is covered, i.e., the radiation dose used can be reduced. In addition, the image quality is improved by reducing of the scattered radiation.

In another advantageous embodiment of the X-ray exposure system according to the invention, the sampling unit is operated to sample the signals of the image receiver surface in order to determine which pixels are illuminated by the radiation beam during a test exposure, and an image of the radiation field on the image receiver is displayed on a monitor so that, using this displayed image, an optimal adjustment of the radiation field to the image plate is enabled by means of manual adjustment of collimators and/or manual displacement and/or alignment of the x-ray radiator.

In the method according to the invention, a patient is subjected to a test exposure, and an image of the outer contours of the patient obtained on the image receiver's active surface is displayed on a display screen together with the image of the radiation field on the image receiver, and the radiation field is matched to the outer contours of the patient using this displayed image. This matching can be carried out manually or semiautomatically by marking on the display screen the desired outer boundaries of the radiation field on the image receiver surface, e.g. using a mouse, with the radiation field subsequently being adjusted accordingly using a motor-driven arrangement for orientating of the x-ray radiator and/or for adjusting the collimators. In this case as well, according to a further embodiment of the inventive method, the matching of the radiation field can be carried out automatically on the basis of electrical image information using a motor-driven arrangement for orienting the x-ray radiator and/or adjusting the collimators of the X-ray source.

DESCRIPTION OF THE DRAWINGS

FIG. 6 is a block circuit diagram of an arrangement for controlling positioning of the X-ray beam in a mobile system in accordance with the invention.

DESCRIPTION OF THE PREFERRED EMBODIMENTS

Figure 1:
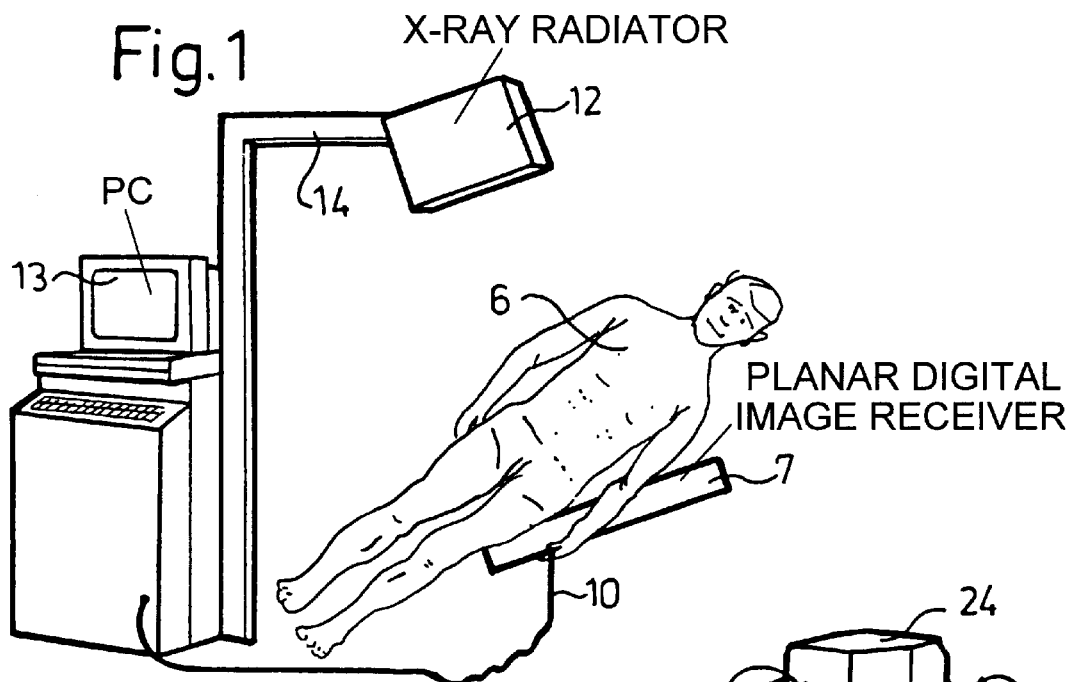
FIG. 1 shows the use of an X-ray system with no mechanical connection between the x-ray source and the radiation receiver.

FIG. 1 shows an X-ray apparatus with a movable x-ray radiator 12 that is carried by an arm 14. The x-ray radiator 12 contains an X-ray source with which an X-ray exposure of a patient 6 can be carried out. A planar digital image receiver 7 for recording the X-ray image is arranged underneath the patient 6. The image receiver 7 has a large number of pixels or picture elements individually having a size of the order of magnitude 100 to 200 μm, and the image plate 7 is connected via a cable 10 with the electronics of the X-ray apparatus for processing the image data. The X-ray apparatus is also equipped with a PC 13. The use of the PC 13 is described in more detail below.

Figure 2:
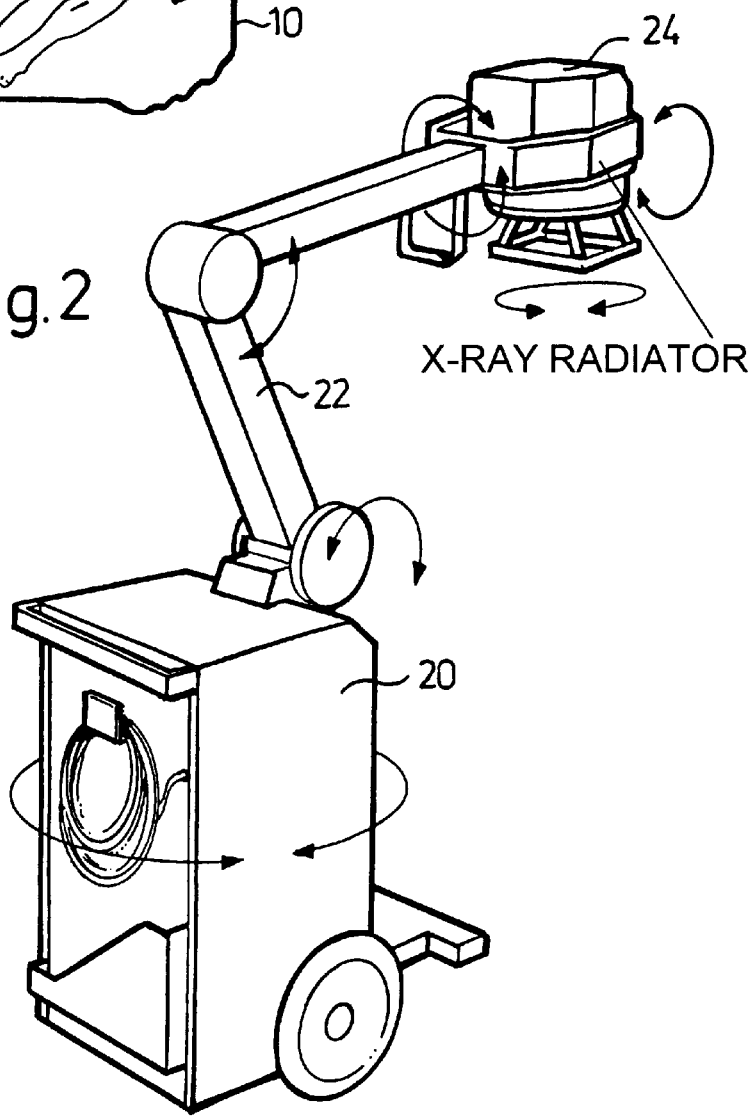
FIG. 2 shows a mobile X-ray source apparatus in the various directions in which the x-ray radiator can be moved.

FIG. 2 shows a mobile X-ray apparatus 20. The apparatus according to the invention can be used in connection with this X-ray apparatus 20. The mobile X-ray apparatus 20 is normally provided in order to be rolled to the bed of a patient when an X-ray exposure is to be produced. The various types and directions of movement for moving the apparatus 20 and the arm 22 thereof that carries the x-ray radiator 24, as well as for moving the x-ray radiator 24 itself in order to adjust the X-ray beam, are shown in FIG. 2 by arrows.

Figure 3:
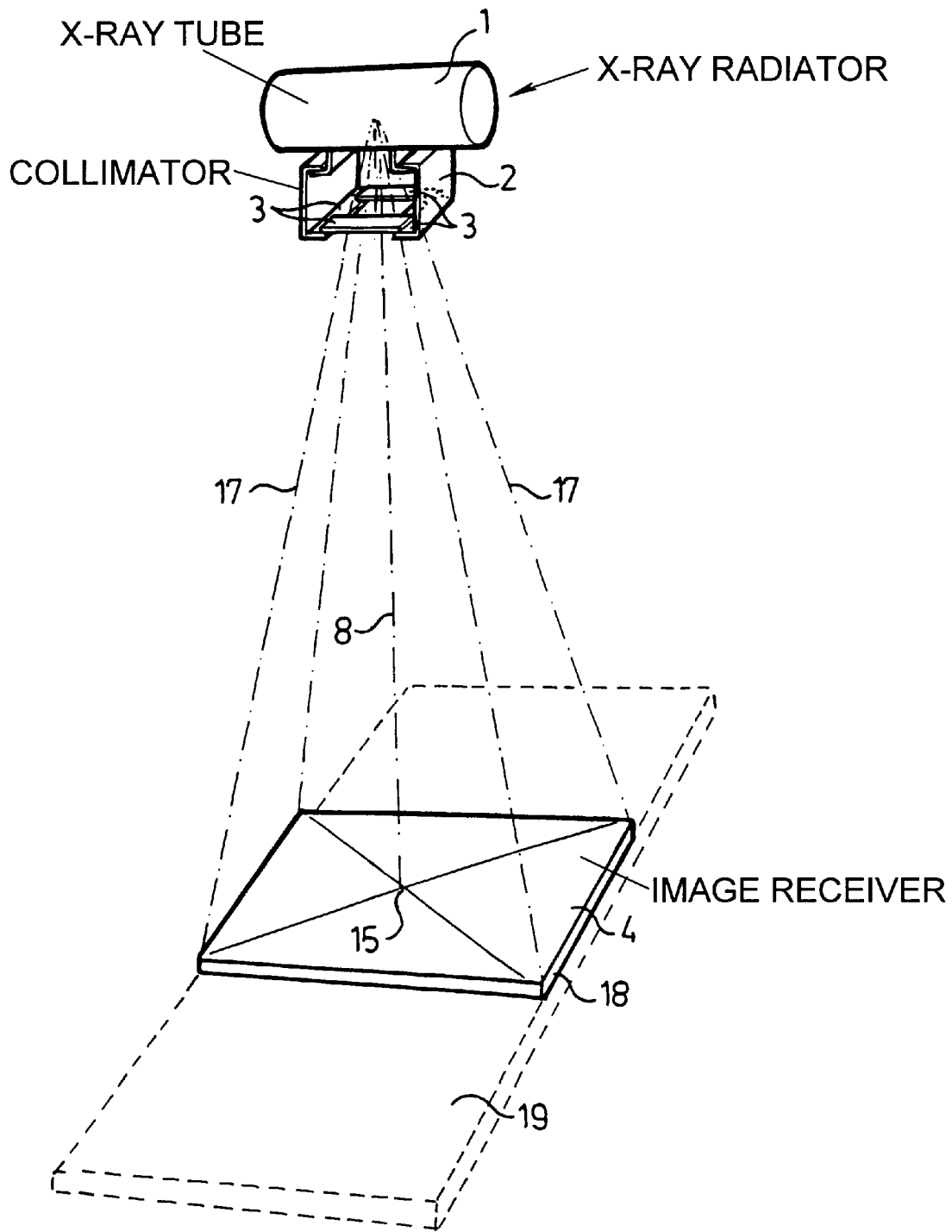
FIG. 3 schematically shows how an X-ray source that illuminates a planar digital image receiver.

The x-ray radiator 24 contains an X-ray source such as an X-ray tube 1 with a collimator 2 in the form of movable diaphragm plates 3 disposed vertically one under the other, with which a generally rectangular X-ray beam 17 can be formed (gated). This can be seen in FIG. 3. The X-ray beam 17 strikes the digital image receiver 4 that is arranged on an examination table 19. FIG. 3 shows that the beam 17 is oriented in centered fashion on the image receiver 4 and its angle of incidence is oriented perpendicularly to the image receiver 4, i.e., the center ray 8 strikes perpendicularly to the image receiver 4 in the midpoint 15 thereof.

Figure 4:
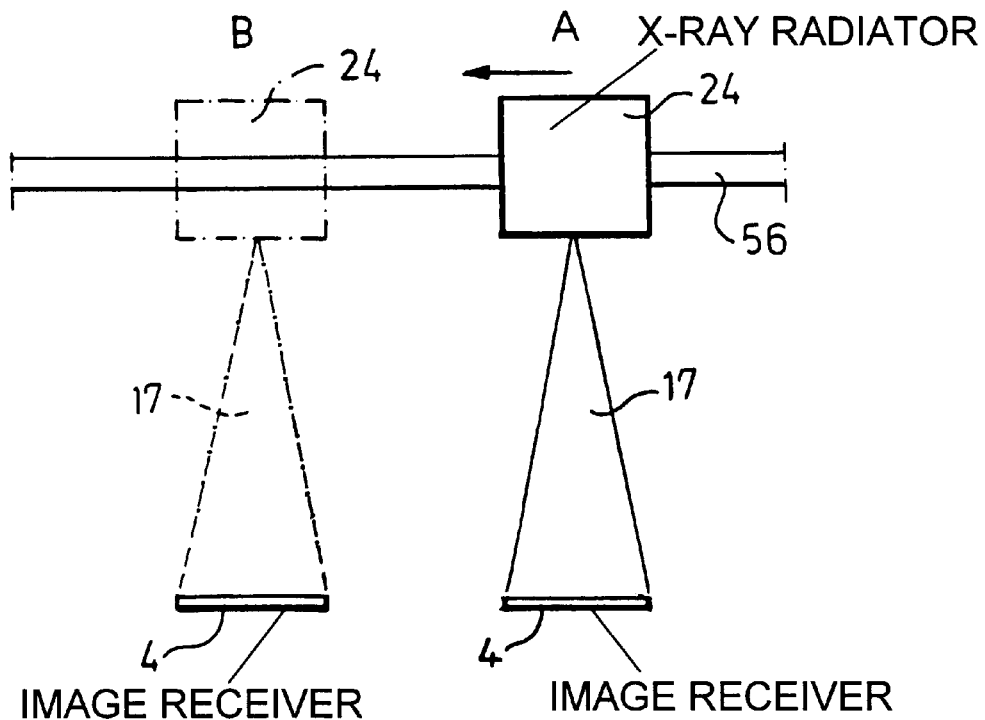
FIGS. 4 and 5 schematically illustrate displacement of an x-ray radiator parallel to the image receiver in two orthogonal directions.
Figure 5:
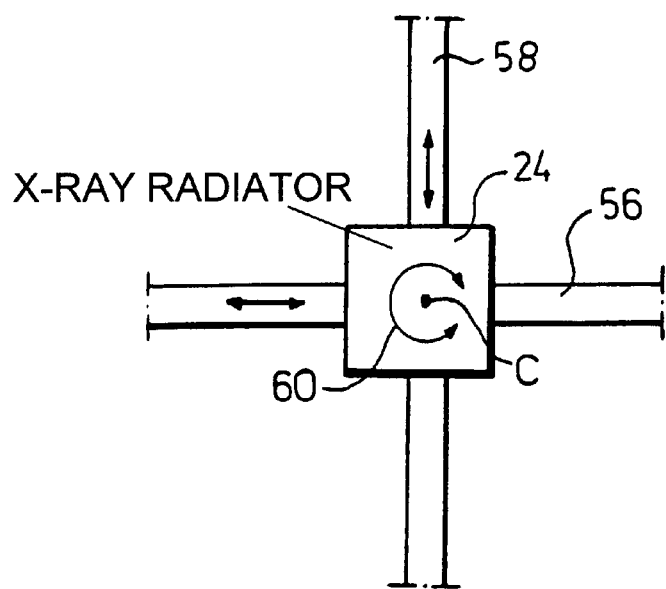

For centering the beam 17 on the image receiver 4, the x-ray radiator 24 can be mounted on mounts 56 and 58, which also enable parallel displacements of the x-ray radiator 24 in two dimensions relative to the image receiver 4, as shown in FIGS. 4 and 5. In FIG. 4, it is accordingly shown how the x-ray radiator 24 is displaced from position A to position B so that the beam is centered on the image receiver 4.

The parallel displacement of the x-ray radiator 24 can be carried out automatically and/or manually.

The mounts 56 and 58, which allowed the x-ray radiator 24 to move in one plane and along two perpendicular directions, are preferably arranged rotatably as a whole about their crossing point C. This is shown in FIG. 5 with the arrow 60.

FIG. 6 schematically shows a digital planar image plate 30 constructed from pixels 32 forming the active receiver surface. Given irradiation with x-radiation, each pixel emits an electrical signal. These signals can be tapped via terminals 34 and are supplied to a sampling unit 36, by means of which it is determined which pixels are irradiated given an exposure of the image receiver 30 by the X-ray beam. Dependent on the signals of the pixels 32 of the image receiver 30, the sampling unit 36 emits control signals to a displacement and rotation control unit 38 for controlling the parallel displacement of the x-ray radiator 40 in space, as well as to a collimator adjustment controlling unit 42 for controlling the adjustment of the collimators 44 for the X-ray source 43 of the x-ray radiator 40. The x-ray beam is thus oriented in space by adjusting its position and/or size. In a test exposure of the image receiver 30, an optimal orientation of the X-ray beam relative to the image receiver 30 is thus enabled in this way, using the pixel signals produced in the test exposure.

The collimators 44 are preferably motor-driven, whereby the collimator adjustment controlling unit 42 controls a collimator motor 46 dependent on a sensed exposure of the pixels 32 of the image receiver 30. The displacement and rotation control unit 38 also preferably controls a motor-driven drive unit 48 for the automatic displacement and orientation of the x-ray radiator 40 dependent on a sensed exposure of the image receiver 30.

A display screen 50 can be connected to a sampling unit 36, in order to display on the display screen 50 an image of the radiation field on the image receiver 30. In this embodiment, on the basis of the image shown in the display screen 50, the collimators can be adjusted and the x-ray radiator 40 can be manually displaced and/or oriented, so that an optimum adjustment of the X-ray field to the image receiver 30 is obtained. In a practical embodiment, the display screen 50 is preferably a screen of a PC (referenced 13 in FIG. 1), to which the image information from the image receiver 7 is supplied via the cable 10.

Figure 7A:
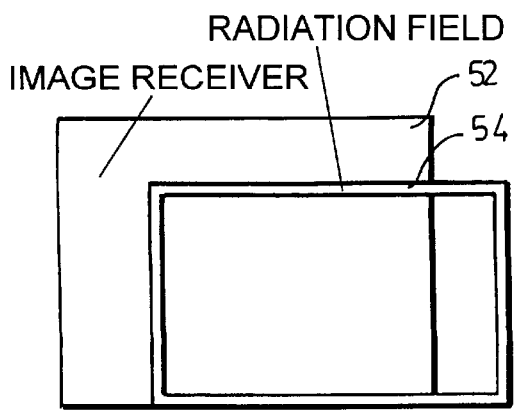
FIGS. 7a, 7b and 8a, 8b and 9a and 9b show examples of the matching of the X-ray beam to the active part of the image receiver using the inventive system of FIG. 6.
Figure 7B:
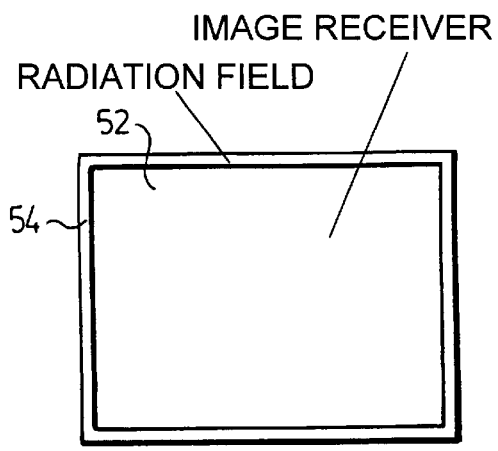
Figure 8A:
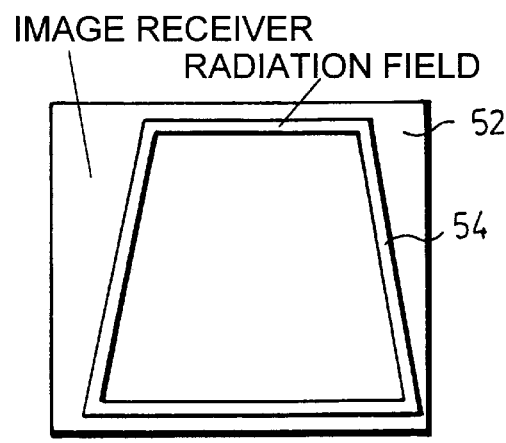
Figure 8B:
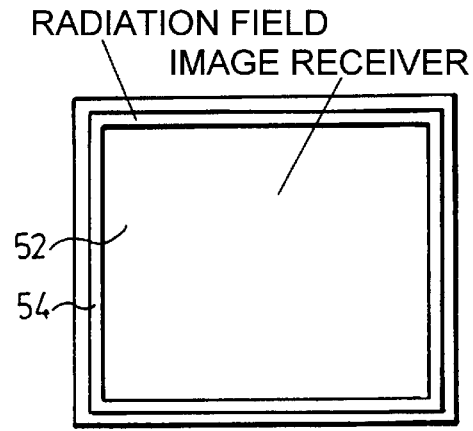

FIGS. 7 and 8 show examples of the image receiver 52 with radiation it being desired that the X-ray beam should illuminate substantially the entire digital image receiver 52. In FIGS. 7a and 8a, it is shown by means of a test exposure how the radiation field is located in relation to the image receiver 52 after the operator first directs the x-ray radiator 40 toward the exposure cartridge but before the matching of the radiation field, which is possible with the apparatus according to the invention, has been carried out. The outer boundary of the radiation field is shown with the lines 54.

From FIG. 7a, it can be seen that the radiation field in this case is partially incorrectly positioned in comparison with the image receiver 52, and partly requires a size adjustment. By means of a parallel displacement of the radiation field, as well as (as described above) a change in the size by adjusting the collimators of the X-ray source, a position as shown in FIG. 7b is activated, in which the shape, size and position of the radiation field agrees completely with the shape, size and position of the image plate 52.

FIG. 8a shows a trapezoidal image 54, obtained in a test exposure, of the radiation field, resulting from one part of the exposure cartridge lying closer to the x-ray radiator 40 than does the another part, so that a rotation of the x-ray radiator 40 for a correction is required. After a rotation of the x-ray radiator 40, as described above, the position shown in FIG. 8b is achieved, i.e., the shape, size and position of the radiation field agree with the shape, size and position of the image plate 52.

Figure 9A:
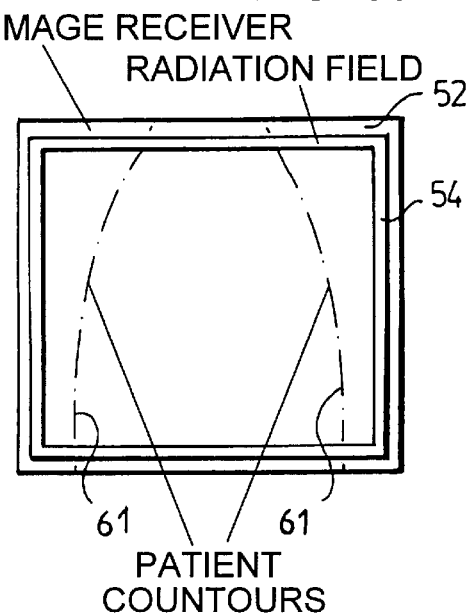
Figure 9B:
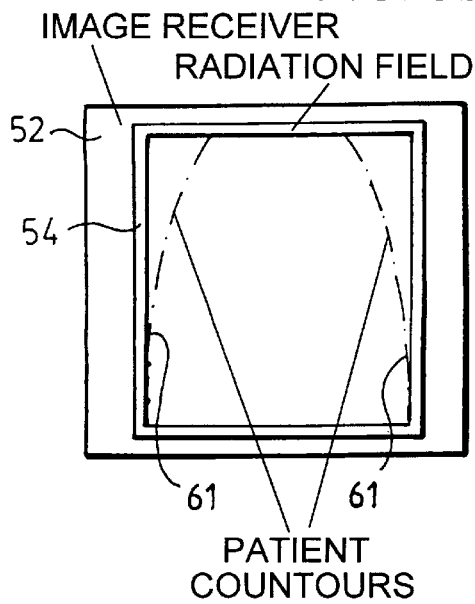

In FIG. 9a, the outer contours 61 of a patient are shown on the image plate 52. By means of the invention, the extension of the radiation field can subsequently be reduced so that it precisely covers the current part of the patient (cf. FIG. 9b). By this means, the radiation dose is reduced to a dose only as large as is absolutely necessary for the current X-ray exposure. As described above, the adjustment of the radiation field to the image receiver 52 in the examples shown in FIGS. 7a to 9b can take place fully automatically or manually, according to predetermined rules, without requiring operator intervention other than physically moving the x-ray radiator 40, by recording on a display screen an image of an image receiver and a radiation field, so that given manual adjustments a feedback is obtained, i.e., so that the effects of the adjustments can be observed on the display screen. The adjustment of the radiation field can also ensue semiautomatically, by marking the position of the outer boundaries 54 on the display screen, e.g. using a mouse, or with the use of a touch screen. Subsequently, the radiation field is adjusted according to corresponding signals by means of motor-driven means for displacement and orientation of the x-ray radiator and/or adjustment of the collimators.

It is described above that the adjustment of the radiation field takes place by means of the adjusting of the collimators of the X-ray source and by means of parallel displacement and/or rotation of the x-ray radiator. It was thereby assumed that the distance between the x-ray radiator and the image receiver is constant. Of course, this distance can also be varied for the purpose of changing the radiation field on the image receiver.

The invention has been described above in connection with a mobile X-ray apparatus, but the invention can of course also be used in connection with stationary X-ray installations. In particular, the adjustment of the radiation field, described in connection with FIG. 9, in which the part of the patient that is of interest has been adjusted precisely, is also of great value given stationary X-ray installations, since the patient is not unnecessarily exposed to a high dose of radiation.

Dental radiography is also an important field of use for the invention, since there is no mechanical connection between the X-ray source and the image receiver, and it cannot be seen visually how the X-ray beam will strike the image receiver. For this reason, in current technology an oversized radiation field is set that is sufficiently large that the image plate will certainly be struck. This is avoided with the invention.

Although various minor modifications might be suggested by those skilled in the art, it should be understood that my wish to embody within the scope of the patent warranted hereon all such modifications as reasonably and properly come with the scope of my contribution to the art.

I claim as my invention:

1. An x-ray exposure system comprising:
   an x-ray radiator containing an x-ray tube which emits an x-ray beam, and having a collimator for gating said x-ray beam;
   beam orienting means for positioning at least one of said x-ray radiator and said collimator for orienting said x-ray beam in space;
   a planar, digital image receiver comprised of a plurality of pixels, said image receiver having no mechanical connection to said x-ray radiator;
   sampling means for sampling electrical signals respectively generated by said pixels of said image receiver when irradiated by said x-ray beam in a test exposure for identifying pixels irradiated by said x-ray beam and for generating a sampled signal dependent on which of said pixels are irradiated; and
   at least one control means, supplied with said sampled signal, for supplying a control signal, dependent on said sampled signal, to said beam orienting means for orienting said x-ray radiator relative to said image receiver for causing said x-ray beam to be incident exclusively on a selected region of said image receiver.

2. An x-ray exposure system as claimed in claim 1 wherein said beam orienting means comprises a motor having a driving connection to said collimator for adjusting a position of said collimator to define a size of said x-ray beam, and wherein said control means comprises means for operating said motor dependent on said sampled signal.

3. An x-ray exposure system as claimed in claim 1 wherein said beam orienting means comprises at least one motor with a driving connection to said x-ray radiator for moving said x-ray radiator, and wherein said control means comprises means for operating said motor for moving said x-ray radiator dependent on said sampled signal.

4. An x-ray exposure apparatus as claimed in claim 1 wherein said beam orienting means comprises means for translationally displacing said x-ray radiator relative to said image receiver.

5. An x-ray exposure apparatus as claimed in claim 1 wherein said beam orienting means comprises means for translationally rotating said x-ray radiator relative to said image receiver.

6. An x-ray system as claimed in claim 1 wherein said beam orienting means comprises means for moving said x-ray radiator toward and away from said image receiver.

7. An x-ray system as claimed in claim 1 wherein said x-ray beam has an outermost contour and wherein said image receiver has an active region having outer-most boundaries, and wherein said sampling means comprises means for identifying said outermost contour of said x-ray beam during said test exposure by identifying outermost pixels in said active region which are irradiated by said x-ray beam, said sampling means, via said sampled signal, causing said control means to operate said beam orienting means for causing said outermost contour of said x-ray beam to substantially coincide with said outer boundaries of said active region of said image receiver.

8. An x-ray exposure system as claimed in claim 1 for use in irradiating a patient during said test exposure, said patient having outer contours, and wherein said sampling means comprises means for identifying said outer contours of said patient during said test exposure, and said sampling means, via said sampled signal, controlling said control means for causing said beam orientation means to match said x-ray beam to said outer contours of said patient.

9. An x-ray exposure system comprising:

an x-ray radiator containing an x-ray tube which emits an x-ray beam, and having a collimator for gating said x-ray beam;

beam orienting means for positioning at least one of said x-ray radiator and said collimator for orienting said x-ray beam in space;

a planar, digital image receiver comprising a plurality of pixels, said image receiver having no mechanical connection to said x-ray radiator;

sampling means for sampling electrical signals from the respective pixels of said image receiver for identifying pixels irradiated by said x-ray beam in a test exposure, said sampling means generating a sampled signal dependent on which of said pixels are irradiated; and display means, supplied with said sampled signal, for displaying an image of a field of said x-ray beam on said image receiver for allowing manual positioning, using said means for positioning, of at least one of said x-radiator and said collimator for orienting said x-ray beam relative to said image receiver.

10. An x-ray exposure apparatus as claimed in claim 9 wherein, during said test exposure, said x-ray beam irradiates a patient, and wherein said sampling means comprises means for including identification of a contour of said patient in said sampled signal, and wherein said display means comprises means for displaying said contour of said patient for use in orienting said x-ray beam relative to said radiation receiver.

11. A method for orienting an x-ray beam relative to a planar, digital image receiver, in an x-ray exposure system having an x-ray radiator containing an x-ray tube which emits said x-ray beam and having a collimator for gating said x-ray beam, with no mechanical connection between said image receiver and said x-ray radiator, and said image receiver comprising a plurality of pixels, said method comprising the steps of:

conducting a test exposure with a patient disposed between said x-ray radiator and said image receiver, said patient having an outer contour;

producing an output signal from said radiation receiver during said test exposure identifying, from pixels irradiated by said x-ray beam in said test exposure, said outer contour of said patient;

supplying said output signal to a display screen and displaying an image of said contours on said display screen together with an image of a radiation field of said x-ray beam on said image receiver; and matching said radiation field of said x-ray beam on said image receiver to said outer contour using said image of said radiation field and said image of said outer contours on said display screen.

12. A method as claimed in claim 11 wherein the step of matching said radiation field of said x-ray beam on said image receiver to said outer contours of said patient comprises manually orienting said x-ray beam for positioning for matching said radiation field to said outer contours.

13. A method as claimed in claim 11 comprising the additional steps of:

marking selected outer boundaries of said radiation field on a display screen of said means for displaying; and in the step of matching said radiation field of said x-ray beam on said image receiver to said outer contour of said patient, automatically orienting said x-ray beam by at least one of adjusting said collimator with a first motor and moving said x-ray radiator with a second motor for matching said radiation field to said outer contour.

14. A method as claimed in claim 11 wherein the step of matching said radiation field of said x-ray beam to said outer contour of said patient comprises automatically orienting said x-ray beam so that said image of said radiation field and said image of said patient contour match.

* * * * *